(12) United States Patent
Reiss (10) Patent No.: US 7,537,610 B2
(45) Date of Patent: May 26, 2009

(54) METHOD AND SYSTEM FOR CREATING A TEXTURED SURFACE ON AN IMPLANTABLE MEDICAL DEVICE

(75) Inventor: Paul Reiss, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 83 days.

(21) Appl. No.: 10/886,788

(22) Filed: Jul. 7, 2004

(65) Prior Publication Data

US 2004/0249444 A1 Dec. 9, 2004

Related U.S. Application Data

(62) Division of application No. 09/752,497, filed on Dec. 27, 2000, now Pat. No. 6,913,617.

(51) Int. Cl.
*A61F 2/06* (2006.01)
(52) U.S. Cl. ............... 623/1.39; 623/1.15; 427/2.24
(58) Field of Classification Search ....... 623/1.39–1.42, 623/1.44–1.48; 427/2.25, 2.24
See application file for complete search history.

(56) References Cited

U.S. PATENT DOCUMENTS

| | | | |
|---|---|---|---|
| 4,147,425 A | 4/1979 | Friedman et al. | |
| 5,245,152 A * | 9/1993 | McCall | 219/69.14 |
| 5,824,048 A | 10/1998 | Tuch | |
| 5,843,172 A | 12/1998 | Yan | |
| 5,972,027 A | 10/1999 | Johnson | |
| 6,107,004 A * | 8/2000 | Donadio, III | 430/320 |
| 6,225,589 B1 * | 5/2001 | Bartok | 219/69.15 |
| 6,379,381 B1 * | 4/2002 | Hossainy et al. | 623/1.42 |
| 6,410,877 B1 | 6/2002 | Dixon et al. | |
| 6,506,437 B1 * | 1/2003 | Harish et al. | 427/2.25 |
| 6,558,733 B1 * | 5/2003 | Hossainy et al. | 427/2.24 |
| 6,758,859 B1 * | 7/2004 | Dang et al. | 623/1.15 |
| 6,805,898 B1 * | 10/2004 | Wu et al. | 427/2.25 |
| 2004/0024449 A1 * | 2/2004 | Boyle | 623/1.42 |
| 2004/0225347 A1 * | 11/2004 | Lang | 623/1.15 |

FOREIGN PATENT DOCUMENTS

EP 0 687 008 12/1995

* cited by examiner

*Primary Examiner*—Bruce E Snow
(74) *Attorney, Agent, or Firm*—Squire, Sanders & Dempsey, L.L.P.

(57) ABSTRACT

A method for forming an implantable medical device, such as a stent, is provided, in which electric discharges are applied to a metal surface of the implantable medical device. The electric discharges pit the surface. The pitted surface improves retention of a coating on the device and increases the amount of coating that can be carried by the device. An electric discharge machining process is described for applying electric discharges to the surface of the implantable medical device or portion thereof.

14 Claims, 6 Drawing Sheets

METHOD AND SYSTEM FOR CREATING A TEXTURED SURFACE ON AN IMPLANTABLE MEDICAL DEVICE

CROSS REFERENCE

This is a divisional application of U.S. Ser. No. 09/752,497, which was filed on Dec. 27, 2000 now U.S. Pat. No. 6,913,617.

BACKGROUND OF THE INVENTION

1. Field of the Invention

This invention relates generally to methods for forming surface features of implantable medical devices. More particularly, the present invention is directed to methods of using electric discharges to roughen the surface of implantable medical devices, such as stents and grafts, with numerous pits.

2. Description of the Background

Percutaneous transluminal coronary angioplasty (PTCA) is a procedure for treating heart disease. A catheter assembly having a balloon portion is introduced into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against and remodel the artery wall for dilating the lumen. The balloon is then deflated to a smaller profile to allow the catheter to be withdrawn from the patient's vasculature.

Following the PTCA procedure, however, damage to the arterial lining can potentially cause re-occlusion of the artery, due to thrombosis, restenosis, or collapse of the arterial walls. To reduce the partial or total occlusion of the artery, an implantable device, an example of which includes an expandable stent, is implanted in the lumen to maintain the vascular patency. Stents are scaffoldings, usually cylindrical or tubular in shape, functioning to physically hold open, and if desired, to expand the wall of the passageway. Stents are inserted into an anatomical passageway and operate to physically hold open and, if desired, to expand or replace the wall of a passageway. Stents are capable of being compressed for insertion through small cavities via balloon-catheters, positioned in a desired location, then expanded to a larger diameter. Stents can be either balloon-expandable or self-expanding. Examples in patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

To further fight against thrombosis and restenosis, and in treating the damaged vascular tissue, therapeutic substances can be administered. For example, anticoagulants, antiplatelets and cytostatic agents are commonly used to prevent thrombosis of the coronary lumen, to inhibit development of restenosis, and to reduce post-angioplasty proliferation of the vascular tissue, respectively. It is well-known to deliver such therapeutic substances locally; that is, directly to the treatment site rather than through injection into the body (i.e., systemic delivery). Local delivery allows the use of smaller levels of medication, as compared to systemic dosages, because the delivered therapeutic substances are concentrated at a specific site. Local delivery therefore produces fewer side effects and achieves more effective results.

One commonly applied technique for the local delivery of therapeutic substances is through the use of medicated stents. A well-known method for medicating stents involves the use of a polymeric carrier coated onto the body of the stent, as disclosed in U.S. Pat. No. 5,464,650 issued to Berg et al., U.S. Pat. No. 5,605,696 issued to Eury et al., U.S. Pat. No. 5,865,814 issued to Tuch, and U.S. Pat. No. 5,700,286 issued to Tartaglia et al. The therapeutic substances are impregnated in, located on, or provided underneath the polymeric coating for release in situ once the stent has been implanted.

An obstacle often encountered with the use of stent coatings is poor adhesion of the polymeric coating to the surface of a stent. During stent delivery, a poorly adhering coating can be rubbed and peeled off of the stent if the coating contacts an arterial wall while the stent is being moved into position. Also, when a coated stent is expanded in situ, the distortion the stent undergoes as it expands can cause the coating to peel, crack, or tear, and disengage from the stent. Poor adhesion of the coating material can promote thrombosis and restenosis, by providing additional surfaces for platelets and other blood components to adhere. Additionally, poor adhesion and loss of the coating also leads to loss of a significant amount of the drugs to be delivered from the coating.

Another technical challenge in using stent coatings to deliver drugs is loading enough drug onto the stent, so that an effective amount of the drug or drug combination is delivered to the treatment site. The total amount of a drug that can be loaded onto a stent in a polymeric coating is limited by the amount of drug that can be mixed into the polymer (the concentration of the drug in the polymer), and the amount of polymer and drug mixture that can be coated onto the stent (the thickness of the coating on the stent for a given stent size). Therefore, a stent that carries more coating can deliver greater amounts of drugs. However, increasing the thickness of a stent coating can be difficult, particularly if the coating does not adhere well to the stent material.

One approach to increasing the drug delivery capability of a stent is to provide a pattern of pores, called depots herein, in the polished outer surface of the stent. The depots are cavities that have a depth typically equal to about 40% to 60% of the stent's thickness. The depots can be filled with therapeutic substance for release from the stent.

Notwithstanding the development of such depots, it remains a goal of practitioners to further increase the amount of drugs that are delivered from a stent and develop methods and improve the retention of coatings applied to a stent.

SUMMARY

An implantable medical device capable of delivering therapeutic substances from a coating is provided, along with a method of preparing the device. In comparison to a conventional implantable medical device, the implantable medical device of the present invention can better retain a coating and allow a greater total amount of coating to be carried by the device, thereby allowing for greater amounts of therapeutic substances to be delivered from the device.

In one embodiment of a method of manufacture within the present invention, electric discharges are applied to a designated region of a surface of the implantable medical device. When the electric discharges strike the surface of the implantable medical device, material that forms the surface of the device vaporizes, leaving pits or voids, which cause the surface to be rough.

In various embodiments, the pitted region of the surface, or a portion thereof, can be coated with a coating containing a therapeutic substance or substances, a polymer, or a combination of therapeutic substances and polymer. The coating can be made of one or more layers and the various layers can include different therapeutic substances, polymers, or combinations of therapeutic substances and polymers. The pitted surface has a greater surface area than a smooth surface, allowing for more coating to adhere to the surface, and provides a better mechanical hold for the coating, thereby improving coating retention.

In one embodiment, the electric discharges are applied to the surface using an electric discharge machining process. A discharge electrode and the implantable medical device are placed in a dielectric fluid. The discharge electrode is positioned so as to face a portion of the designated region of the implantable medical device. The discharge electrode and implantable medical device are charged with opposite polarities and an electric discharge is generated between them. The resulting arcs pit the surface of the device.

The discharge electrode can be cylindrical, and can be rotated while applying the electric discharge to the implantable medical device. The discharge electrode can also be tapered to a point, which allows electric discharges to be applied to specific locations on the surface of the implantable medical device.

The type of implantable medical device treated in accordance with the various embodiments of the invention may vary. For example, the implantable device may be a stent or a graft, and may have a plurality of pre-formed depots in the surface.

These and other features and aspects of the various embodiments of the present invention may be better understood in view of the drawings and the following detailed description.

DETAILED DESCRIPTION

Implantable Medical Device

The present invention provides a method for treating the surface of an implantable medical device, such as a stent or graft, which are often referred to as endoprostheses. Beyond stents and grafts, however, other implantable medical devices, such as artificial joints, bones, pacemakers, and the like, may be made in accordance with the methods of the present invention and used for drug delivery. In the discussion below, the example of a stent is provided. Practitioners will appreciate, however, that the methods and structures of the present invention are not limited to a stent, but rather extend to all implantable devices having a metallic surface upon which a coating can be deposited.

Figure 1A:
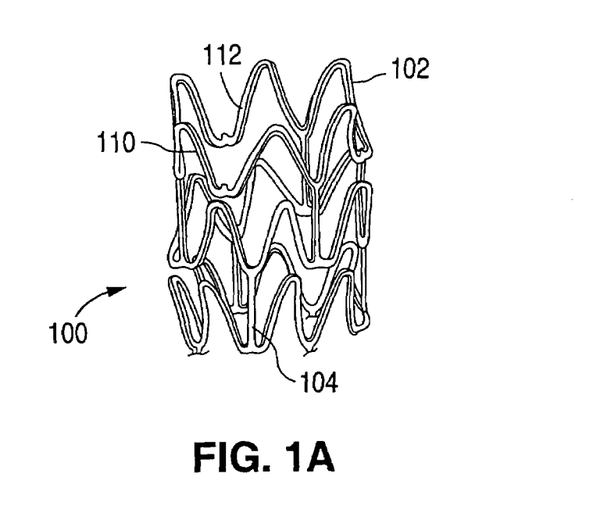
FIG. 1A is a perspective view of an example of a stent in an expanded state.
Figure 1B:
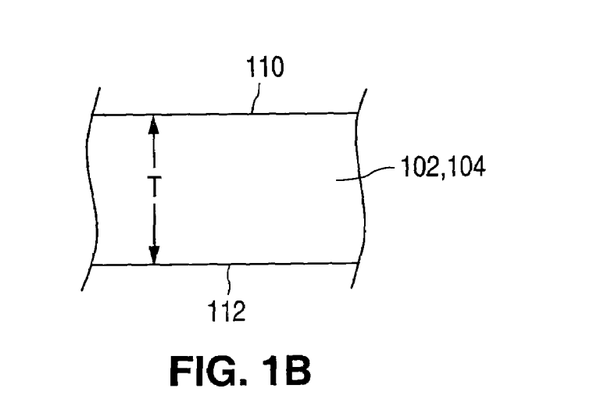
FIG. 1B is a sectional view of a stent strut.
Figure 1C:
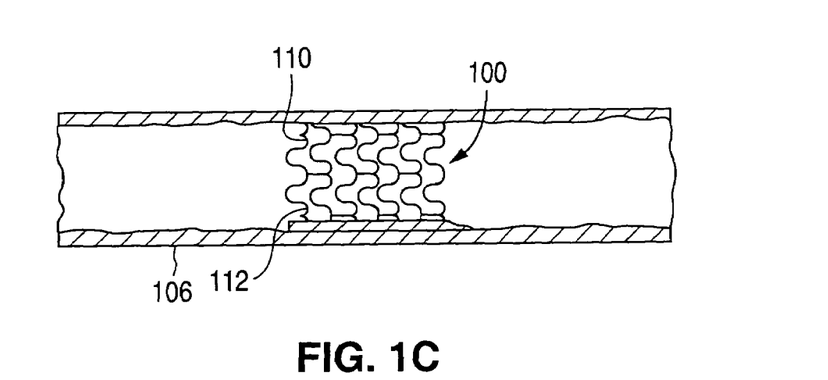
FIG. 1C is a sectional side view of a conventional stent implanted in a lumen.

FIGS. 1A-1C illustrate an exemplary stent 100 in accordance with one embodiment of the present invention. Exemplary stent 100 is a patterned tubular device that includes a plurality of radially expanding cylindrical struts 102 disposed generally coaxially. Connecting struts 104 disposed between adjacent cylindrical struts 102 interconnects the cylindrical struts 102. FIG. 1B is a cross-sectional view through strut 102, 104. Struts 102 and 104 have a suitable thickness T between the stent outer surface 110 and inner surface 112. Typically, thickness T is in the range of approximately 50 μm (0.002 inches) to 200 μm (0.008 inches). A specific choice of thickness depends on the anatomy and size of the target lumen. FIG. 1C illustrates stent 100 of FIG. 1A implanted in a lumen 106.

Typical materials used for stent 100 are metals or alloys, examples of which include, but are not limited to, stainless steel, "MP35N," "MP20N," nickel titanium alloys such as Nitinol (e.g., ELASTINITE® by Advanced Cardiovascular Systems, Inc., Santa Clara, Calif.), tantalum, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

In accordance with the present invention, a series of electric discharges are applied to a designated region or regions of the metallic surface of the stent or other implantable medical device. For example, the discharges may be applied to the entire outer surface, the entire inner surface, both outer and inner surfaces, or just a portion of the inner and/or outer surfaces. The electric discharges contact the surface with sufficient energy to vaporize the material on the surface of the implantable medical device, creating numerous pits, sometimes called voids, the combined effect of which is a rough surface having increased surface area.

Figure 2A:
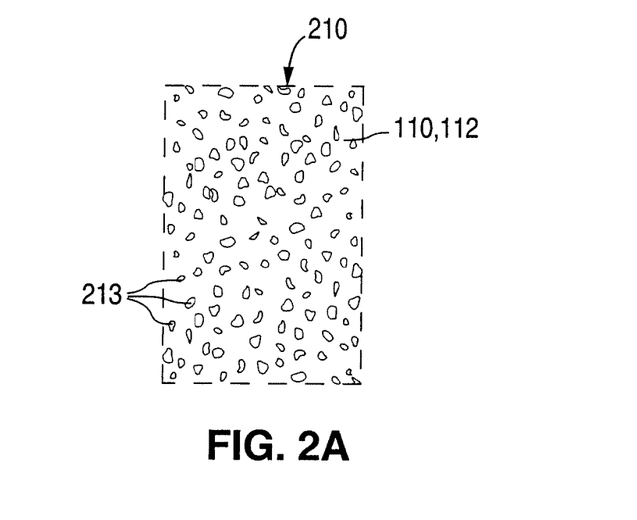
FIG. 2A is a plan view illustrating a portion of the surface of a stent that has been pitted by application of electric discharges.
Figure 2B:
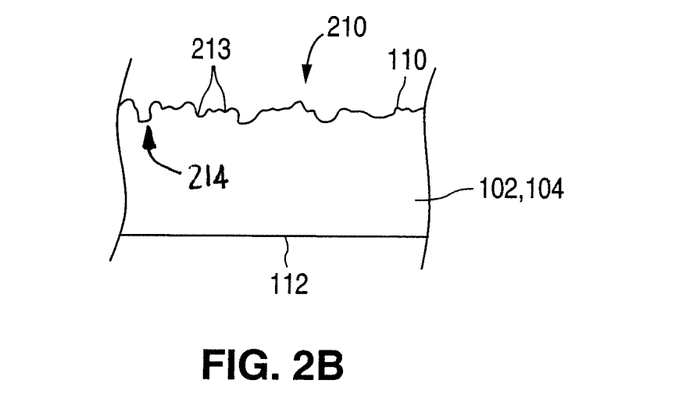
FIG. 2B is a sectional view of a portion of a stent having an outer surface that has been pitted by application of electric discharges.
Figure 2C:
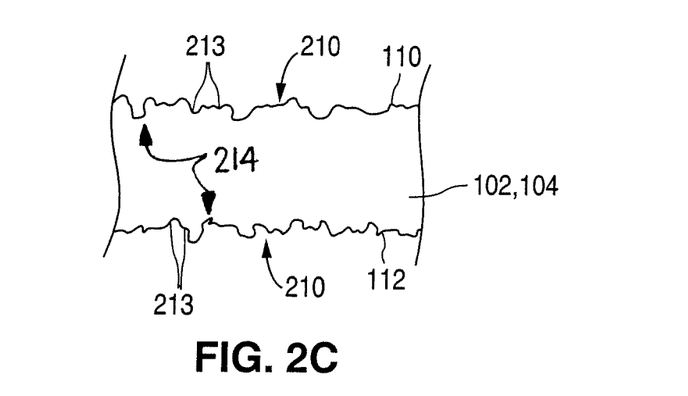
FIG. 2C is a sectional view of a portion of a stent having outer and inner surfaces that have been pitted by application of electric discharge.

FIG. 2A is a plan view illustrating a portion of a designated region 210 of a surface 110, 112 of stent 100. Numerous pits 213 have been formed on the surface 110, 112 by application of the electric discharges. FIG. 2B is a sectional view of stent strut 102, 104 illustrating pits 213 formed in designated region 210 of outer surface 110. FIG. 2C is a sectional view of stent strut 102, 104 illustrating pits 213 formed in designated region 210 of both outer 110 and inner 112 surfaces. Some of the pits 213 include undercuts 214. The size and distribution of the pits of the roughened surface may be controlled by variables affecting the electric discharge or by selection of the electric discharge machining apparatus, as further discussed below.

Figure 3A:
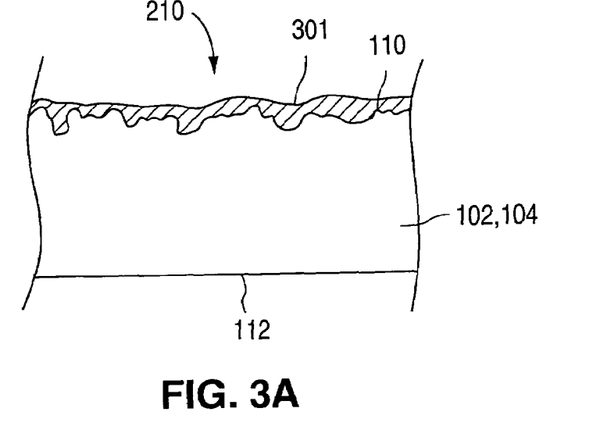
FIG. 3A is the sectional view of the portion of the stent of FIG. 2B with a coating covering the pitted surface.

FIG. 3A illustrates a coating 301 covering designated region 210, shown here as outer surface 110 of stent 100. Coating 301 may be, for example, a polymeric coating that contains a therapeutic substance, as described below. Coating 301 fills and covers pits 213. The pits 213 provide a mechanical hold for the coating and help to prevent the coating from slipping or peeling off of the implantable device.

In addition, because pits 213 increase the surface area of the designated region 210, the amount of coating that can be put onto surface 110 of stent 100 is increased. The greater amount of coating allows the implantable device to carry more therapeutic substance, so more medicine can be delivered from the implantable device in situ.

Figure 3B:
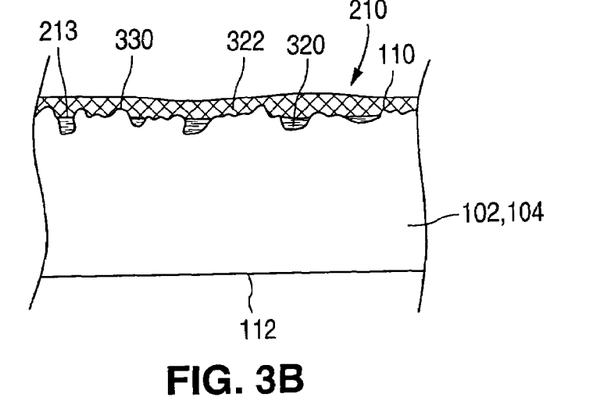
FIGS. 3B and 3C are sectional views of the portions of the stent illustrated in FIG. 2B with two and three layers, respectively, of coatings covering the pitted surface.
Figure 3C:
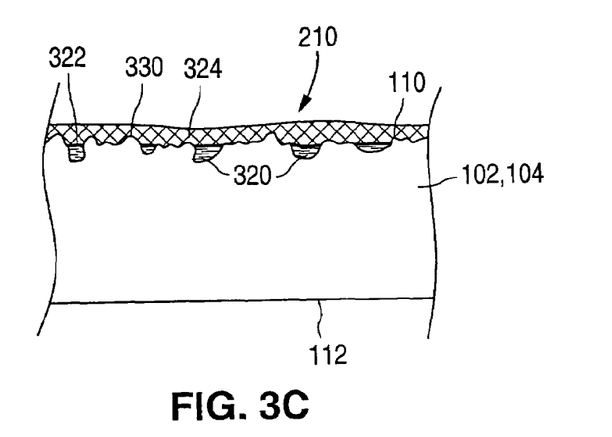

In an alternate embodiment illustrated in FIGS. 3B and 3C, the pitted surface can allow two or more layers of a coating to adhere to surface 110 of designated region 210. A first layer 320 is coated onto the surface and then covered with a second layer, 322, or even third layer 324 (FIG. 3C). The first coating 320 partially fills the deeper area of the pits 213, but portions 330 of the surface 110 extend above the coating 320. A second (and third) layer can adhere to both the first layer and protruding stent material in portions of the pitted surface 110.

The multiple coating layers of FIGS. 3B and 3C can be used to achieve different therapeutic substance release profiles. For example, if it is desired to release two therapeutic substances sequentially, two layers as illustrated in FIG. 3B can be used. For example, a therapeutic substance in the outer layer 322 will be released first, as the outer layer dissolves, and a therapeutic substance in the underlying layer 320 will be released after the outer layer 322 has wholly or partially dissolved. This release profile is sometimes referred to as a "late burst", especially if the second therapeutic substance to be released (that in the underlying layer 320) is in a highly soluble form, for instance, pure crystalline form. In one embodiment, the underlying layer can be made of a material that, for chemical reasons, does not adhere well to the metal surface. In such instances, the outer layer can be used to hold the underlying layer onto the implantable device. As shown in FIGS. 3B and 3C, the outer layer 322, 324 can adhere to portions of the surface not covered by the underlying layer, and thus act as a seal for an underlying layer.

Figure 4A:
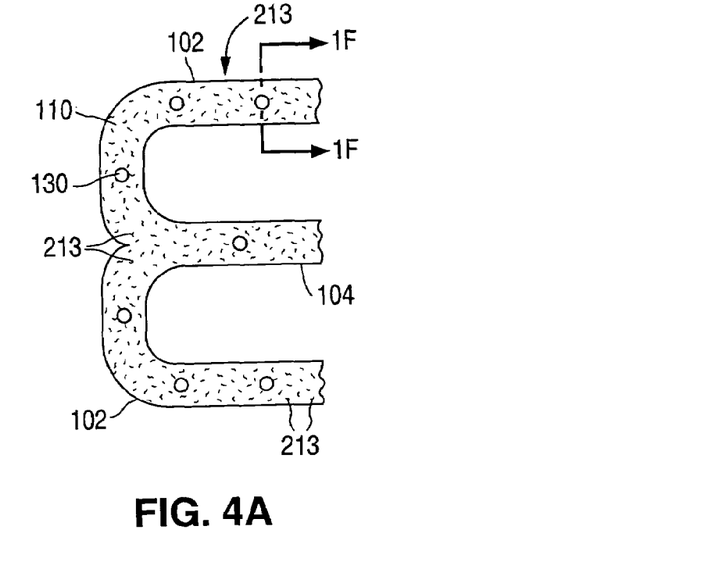
FIG. 4A illustrates a portion of the struts of the stent of FIG. 1A, which shows depots formed therein and wherein the surface of the stent around the depots has been pitted by application of electric discharge.
Figure 4B:
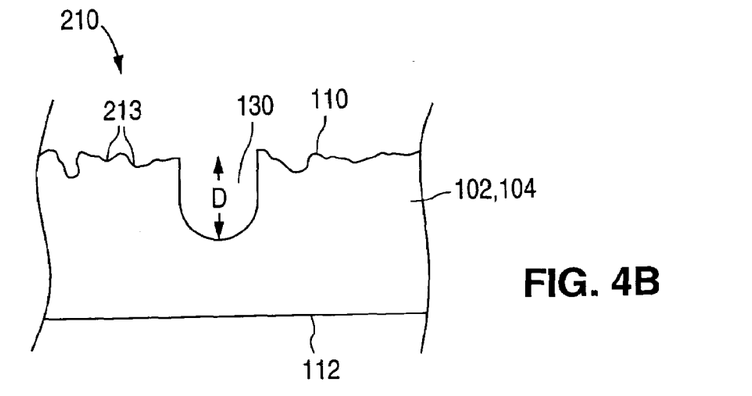
FIG. 4B is a cross-sectional side view of a stent strut, taken in the direction of the arrows and along the plane of line 1F-1F of FIG. 4A, illustrating a depot formed in the stent strut and the pitted surface of the stent strut.

In some embodiments, stent 100 may include depots, also referred to as pores or cavities. FIGS. 4A and 4B illustrate a portion of stent struts 102, 104 of stent 100 having depots 130 in designated region 210 of an outer surface 110. Depots 130 are formed at any pre-selected location and have any preselected depth, size, and geometrical configuration, according to intended usage and application. Depots 130 are formed by methods, such as laser discharge or chemical etching, which are well-known. In general, the depth D (FIG. 4B) and size of depots 130 is much greater than the size of the pits 213 created on the surface 110 by the electric discharge machining process. Depots 130 are also formed on stent 100 in a more regular pattern than pits 213.

Figure 4C:
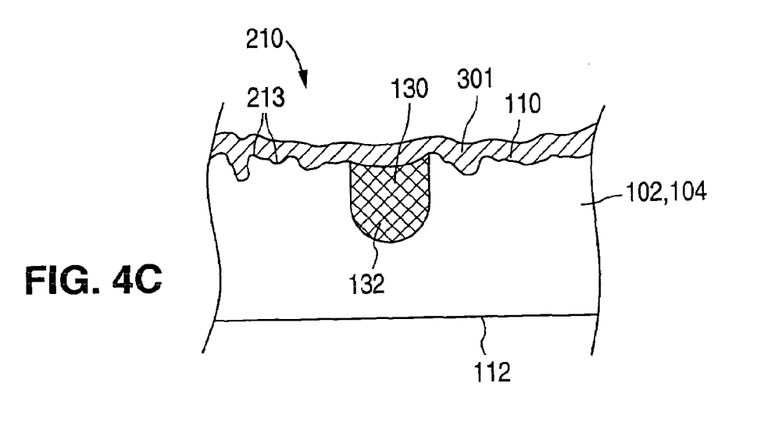
FIG. 4C is a sectional view of a coating over a portion of a stent having pre-formed depots, as shown in FIG. 4A, and also having a pitted surface. The depots are filled with a material. A coating covers the surface roughened by the application of electric discharge and the depots containing the material.

Depots 130 increase the amount of therapeutic substance stent 100 is capable of carrying and delivering. As illustrated in FIG. 4C, depots 130 can be filled with a material 132, e.g., a therapeutic substance, and depot 130 and material 132 can be overlain by a coating 301 that fills and covers pits 213. Material 132 and coating 301 may contain different therapeutic substances and can be used to achieve different release profiles. For example, the depot 130 may be used to create a "late burst" of material 132, as described above with respect to FIGS. 3B and 3C.

Method of Making the Exemplary Stent

A. Forming the Stent

Methods of manufacturing stents are known to those of skill in the art. In general, the electric discharge may be applied to the surface of the stent at any point in the stent manufacturing process, provided that subsequent processing does not remove the pitted surface desired in the completed stent.

For example, in a typical method of making a stent, a thin-walled, small diameter metallic tube is cut to produce the desired stent pattern, using methods such as laser cutting or chemical etching. The cut stent may then be descaled, polished, cleaned and rinsed. In one embodiment, the electric discharge is applied to the outer surface after the stent has been polished. In this case the electric discharge only reaches the outer surface of the stent, so the smooth inner surface is protected. In another embodiment, the electric discharge is applied to the stent material before the stent pattern is cut. In these cases, the pitted surface may need to be preserved when the stent pattern is cut, descaled, and polished, if these processing operations will smooth the pitted surface more than is desired. To protect the pitted surface, a temporary protective coating, for example, a poly (vinyl alcohol) coating, can be applied to the outer surface of the stent before subsequent processing.

If the stent contains depots 130 (FIGS. 4A-4C), the electric discharge can be applied either before or after formation of the depots, depending on the methods used to form the depots. Typically, if depots are formed by a laser in the stent surface before the application of the electric discharge, the series of sparks in the discharge do not reach into the depots, and do not affect the depth and overall shape of the depots.

The application of electric discharges to a surface can be accomplished by electric discharge machining processes, which are known to those of skill in the art. In a typical electric discharge machining process, a discharge electrode is brought into close proximity with the workpiece, which in this case is the stent or other implantable medical device. The discharge electrode and implantable medical device are submerged in a dielectric fluid with a predetermined gap maintained between the two. The discharge electrode and implantable medical device are electrically charged with opposite polarities, and voltage is applied in an amount exceeding the breakdown voltage of the dielectric fluid. The result is a series of electric discharges struck across the gap through the fluid. The electric discharges contact and vaporize the material on the surface of the implantable medical device, thereby pitting the surface.

The electric discharge machining apparatus used for applying electric discharges to a stent or other implantable medical device can have many possible designs. Examples are illustrated in FIGS. 5A-5D.

Figure 5A:
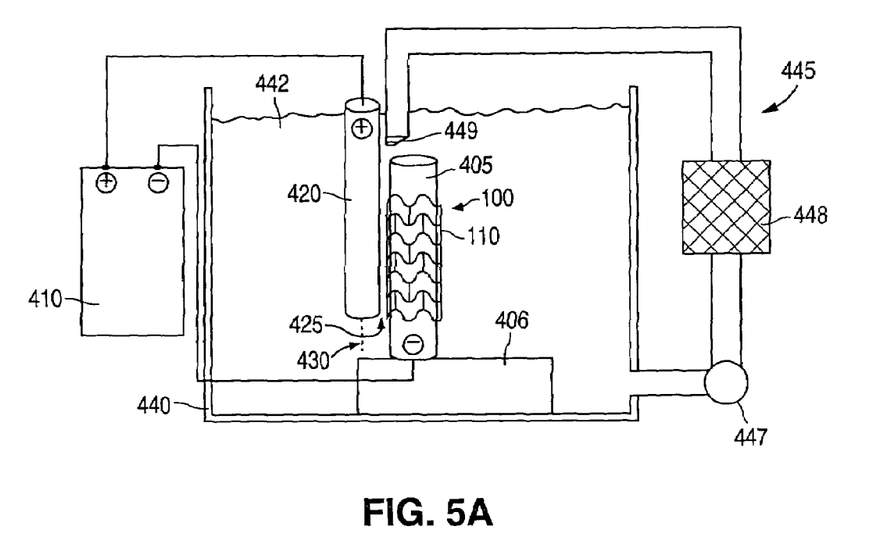
FIGS. 5A, 5B, 5C, and 5D are schematic representations of an electric discharge machining apparatus that can be used to apply electric discharges to the surface of a stent or other implantable medical device.

Referring to FIG. 5A, stent 100 is mounted on a conductive mandrel 405. A motor 406 rotates mandrel 405 at a controlled angular speed. Mandrel 405 is connected to a power source 410, and typically has a negative electric charge. Mandrel 405 and stent 100 are in close contact, so that stent 100 rotates as mandrel 405 is rotated, and so that the electrical charge on mandrel 405 is imparted to stent 100.

The discharge electrode 420 is mounted so that there is a narrow gap 425 between stent 100 and discharge electrode 420. The gap 425 has a typical size of, for example, between 10 μm and 100 μm, typically 77 μm (0.003 inch). The discharge electrode 420 may have a variety of shapes, as discussed below, and may be made from materials that include, but are not limited to, copper, tungsten, various graphites, or metal-matrix-ceramics, such as $ZrBr_2/Cu$.

Both discharge electrode 420 and stent 100 are submerged in a tank 440 containing a suitable dielectric fluid 442, which can be for example, water, glycols, paraffinic mineral oil, naphthenic mineral oil, kerosene, or silicon oils. The dielectric fluid 442 acts as an electrical insulator to help control the electric discharges. The dielectric fluid 442 is typically pumped through the gap 425 to flush away eroded particles between the discharge electrode 420 and stent 100. A recirculation system 445 for the dielectric fluid 442 includes pump 447 to circulate the dielectric fluid, a filter 448 to remove debris from the fluid, and a nozzle 449 to direct the dielectric fluid into the gap 425 at a high pressure.

The discharge electrode 420 is connected to the power source 410 so the electrode 420 is charged with the opposite polarity from the mandrel 405 and stent 100. In this example the discharge electrode 420 is positively charged. As voltage is applied to the discharge electrode 420 and stent 100, electric discharges occur across the gap 425 between the closest faces of discharge electrode 420 and stent 100. If stent 100 is rotated through a complete circle, the entire outer surface 110 of the stent 100 is brought close to discharge electrode 420, resulting in electric discharges striking and roughening the entire outer surface 110.

The operating parameters used to deliver electric discharges to the surface of the implantable medical device can be chosen to create the desired roughness of the surface. The amount of material removed from stent 100 by each electric discharge is proportional to the energy contained in the electric discharge. A higher energy density results in larger pits and in a rougher surface, and can be achieved by increasing the current or voltage level, narrowing the size of gap 425, and increasing the length of time an electric discharge is applied to the stent. The rate at which the stent is rotated can be controlled to affect the pit distribution, which will also affect the roughness of the surface. In general, faster rotation rates result in fewer pits.

Figure 5B:
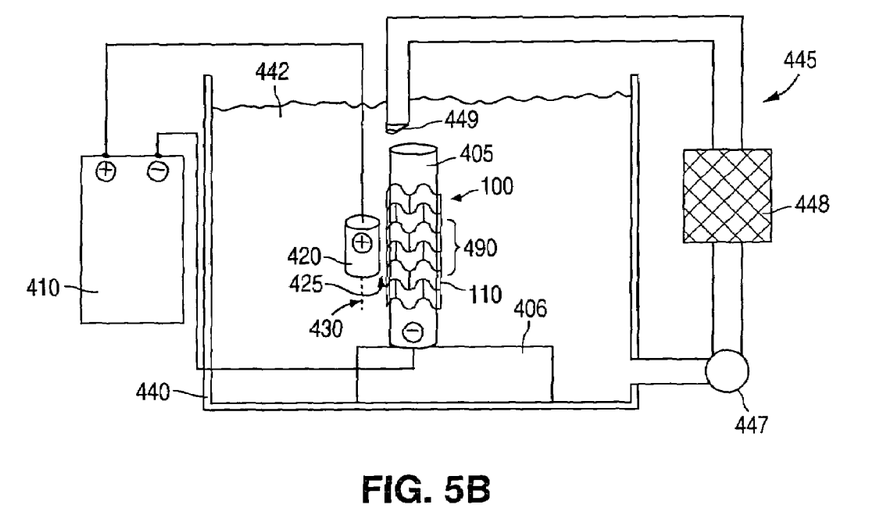

In other embodiments, the shape of the discharge electrode can be different. For example, as illustrated in FIG. 5B, the discharge electrode 420 may be cylindrical and shorter in length than the length of the stent, so that the designated region of the stent that is roughened is in a middle section 490 of the stent 100.

In other embodiments, the shape of the discharge electrode can be different. For example, as illustrated in FIG. 5B, the discharge electrode 420 may cylindrical and shorter in length than the length of the stent, so that the designated region of the stent that is roughened is in a middle section 490 of the stent 100.

Figure 5C:
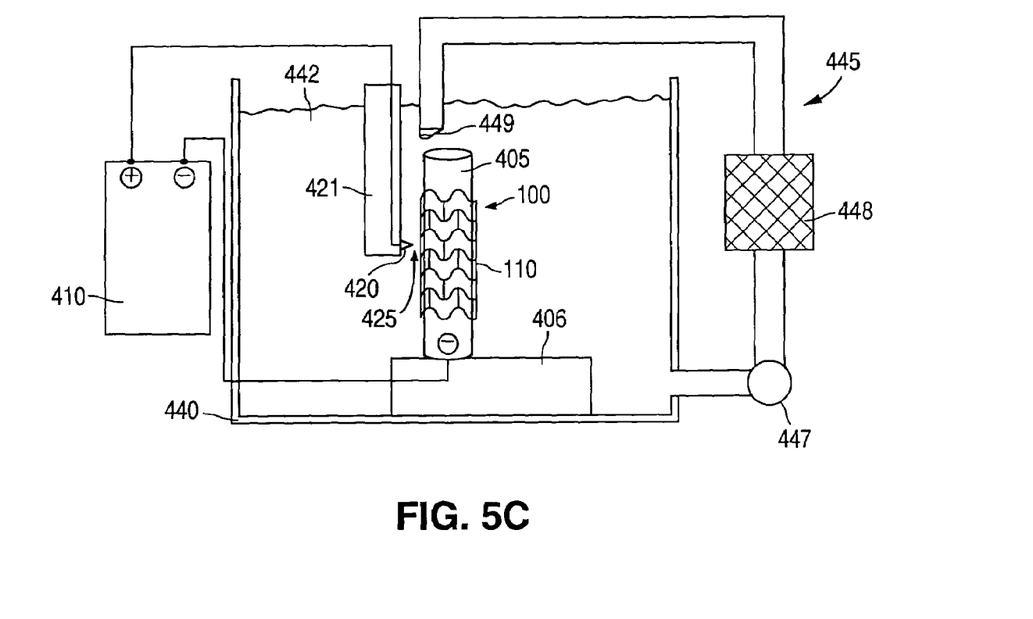

The discharge electrode 420 may also be shaped into a point, as shown in FIG. 5C. The electric discharge always travels the shortest distance, across the narrowest part of the gap between the discharge electrode and the nearest point on the stent. Therefore, if discharge electrode 420 is pointed, electric discharge will leave only the tip of the point and can be delivered to a specific location on the surface of the stent. In this configuration the discharge electrode 420 can be used to create deeper pits, or pores, in the surface of the stent by repeatedly applying electric discharge to the same specific location.

The pointed discharge electrode 420 may be mounted on an automatic controller 421. To deliver electric discharge to a number of specific locations on the outer surface 110, the path of the pointed discharge electrode 420 may be computer controlled to match the pattern of the stent and the desired location of the pits, and to advance the point of the electrode into the pit as it becomes deeper.

Figure 5D:
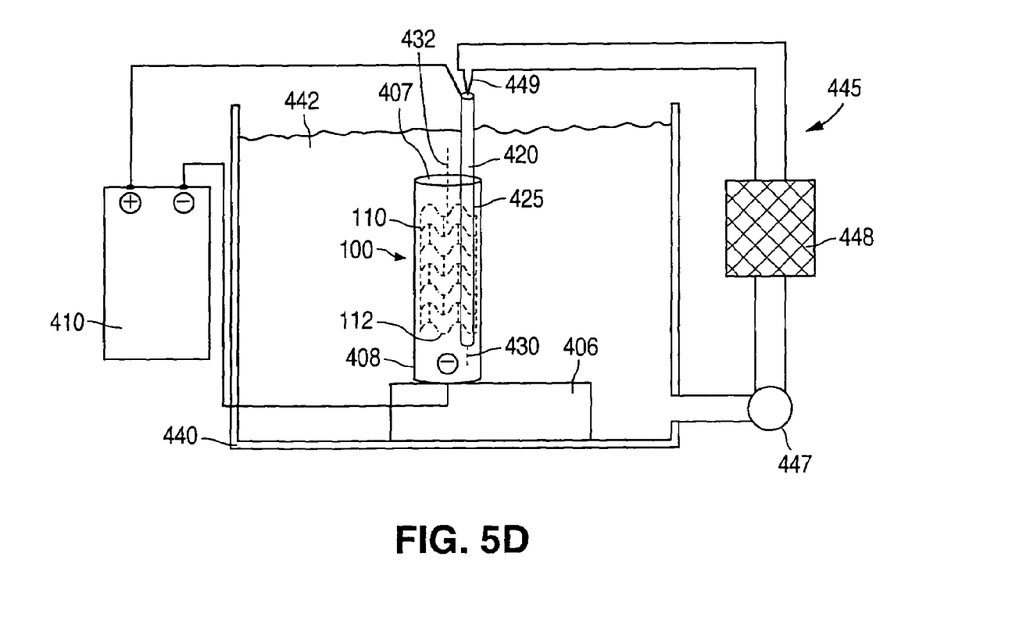

FIG. 5D illustrates an exemplary configuration of an electric discharge machining apparatus used to apply electric discharges to an inner surface 112 of stent 100. Stent 100 is mounted on the inner bore 407 of conductive tube 408, and is in close contact with tube 408 so that electric charge on tube 408 is imparted to stent 100. Discharge electrode 420 is inserted inside tube 408 and stent 100, so that there is a narrow gap 425 between discharge electrode 420 and stent 100. Dielectric fluid 442 can be pumped through gap 442 as previously described. Alternatively, as illustrated in FIG. 5D, dielectric fluid can be pumped into discharge electrode 420, which is hollow and has fluid outlets in it to allow dielectric fluid 442 to leave electrode 420 and fill gap 425.

In the exemplary apparatus of FIG. 5D, discharge electrode 420 is cylindrical, however, discharge electrode 420 can have a variety of other shapes, as previously described. Discharge electrode 420 is rotated about a central axis 430 to present a fresh surface to stent 100. To cover inner surface 112 of stent 100, either tube 408 and stent 100 are rotated about axis 432 while discharge electrode 420 stays in place, or discharge electrode 420 is revolved about axis 432.

B. Coatings for Delivering Therapeutic Substances

Methods of coating a stent or other implantable medical device with one or more therapeutic substances, or with a polymer containing one or more therapeutic substances are well-known. For example, one or more therapeutic substances can be added to stent 100 by dissolving or mixing the therapeutic substances in a solvent and applying the therapeutic substance and solvent mixture to stent 100. To cover stent 100 with a polymer containing the therapeutic substance or substance combination, a solution of the polymeric material and one or more therapeutic substances are mixed, often with a solvent, and the polymer mixture is applied to the implantable device. Stent 100 can also be coated with a polymer that does not contain a therapeutic substance, for example, to form a sealant layer over an underlying layer, which does contain a therapeutic substance.

Methods of applying the therapeutic substance, polymer, or therapeutic substance and polymer mixture to stent 100 include, but are not limited to, immersion, spray-coating, sputtering, and gas-phase polymerization. Immersion, or dip-coating, entails submerging the entire stent 100, or an entire section of stent 100, in the mixture. Stent 100 is then dried, for instance in a vacuum or oven, to evaporate the solvent, leaving the therapeutic substance or therapeutic substance and polymer coating on the stent. Similarly, spray-coating requires enveloping the entire stent, or an entire section of the stent, in a large cloud of the mixture, and then allowing the solvent to evaporate, to leave the coating. Sputtering typically involves placing a polymeric coating material target in an environment, and applying energy to the target such that polymeric material is emitted from the target. The polymer emitted deposits onto the device, forming a coating. Similarly, gas phase polymerization typically entails applying energy to a monomer in the gas phase within a system set up such that the polymer formed is attracted to a stent, thereby creating a coating around the stent.

If stent 100 contains depots (130 of FIGS. 4A-4C), it may desirable to first deposit material (132 of FIG. 4C) into the depots before coating the outer surface of the device, particularly if material 132 differs from the coating material. The process of filling depots 130 is typically different from the process used for coating stent 100, because filling depot 130 with material 132 can be facilitated by using a solvent with a high capillary permeation and low viscosity, to penetrate into depots 130 more quickly and completely. Such a high capillary permeation and low viscosity solvent may be less desirable for coating methods, where a more viscous solvent generally produces a thicker coating.

In one method of filling depot 130, material 132, e.g., a therapeutic substance, polymer, or combination thereof, is added to and dispersed throughout the high capillary permeation and low viscosity solvent, so that material 132 is in a true solution, saturated or supersaturated with the solvent or suspended in fine particles in the solvent. Examples of suitable solvents include, but are not limited to, acetone, ethanol, methanol, isopropanol, tetrahydrofuran, and ethyl acetate. The solvent and material 132 mixture is applied to the implantable device using well-known procedures, such as immersion. The solvent and material 132 mixture is applied for a predetermined period of time, the specific time depending on the capillary permeation and viscosity of the solvent, the volume of depots 130, and the amount of material 132 to be deposited.

After applying the solvent and material 132 for a selected duration, the solvent is removed from stent 100 using conventional techniques, such as evaporation in ambient pressure, room temperature and anhydrous atmosphere and/or by exposure to mild heat (e.g., 60° C.) under vacuum condition. A clustered or gross formation of material 132 may be gathered on the surface of stent 100 after removal of the solvent, and it may be desirable to remove this material. The cluster is generally removed by immersing the device in a non-solvent and agitating the implantable device via mechanical perturbation techniques, such as vortexing or vigorous shaking. The non-solvent can have a low capillary permeation or a contact angle greater than about 90° and a viscosity not less than about 0.5 centipoise so that the non-solvent is not capable of significantly penetrating into depots 130 during the process of agitation. Examples of a suitable non-solvent include, but are not limited to, saturated hydrocarbons or alkanes, such as hexane, heptane, and octane.

The implantable device is rinsed in a rinsing solvent to facilitate dissolution of material 132. The rinsing solvent generally has a low capillary permeation and a viscosity of not less than about 1.0 centipoise and is therefore incapable of significantly penetrating into depots 130 during the rinsing stage. The rinsing is conducted rapidly for example in a range from 1 second to about 15 seconds, the exact duration depending on the solubility of material 132 in the rinsing solvent. Extended duration of exposure of stent 100 to the rinsing solvent may lead to the penetration of the rinsing solvent into depots 130. The rinsing step is repeated, if desired, until all traces of material 132 are removed from the surface of the implantable device. The rinsing solvent removes excess material 132 from the surface of stent 100. Useful examples of rinsing solvents include, but are not limited to, dimethylsulfoxide (DMSO), water, DMSO in an aqueous solution, glyme, and glycerol. The rinsing solvent is removed from stent 100 using conventional techniques. All solvents and non-solvents used in the depot filling process are selected to not adversely affect the characteristics and composition of material 132. Although one method of depositing material 132 into depots 130 has been described here, depots 130 may be filled using any suitable method.

Once the depots have been filled, a coating can be applied to the outer surface of stent 100, as described above.

The polymer used for coating stent 100 and filling depots is typically either bioabsorbable or biostable. A bioabsorbable polymer bio-degrades or breaks down in the body and is not present sufficiently long after implantation to cause an adverse local response. Bioabsorbable polymers are gradually absorbed or eliminated by the body by hydrolysis, metabolic process, bulk, or surface erosion. Examples of bioabsorbable, biodegradable materials include but are not limited to polycaprolactone (PCL), poly-D,L-lactic acid (DL-PLA), poly-L-lactic acid (L-PLA), poly(lactide-co-glycolide), poly (hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly(amino acids), cyanoacrylates, poly(trimethylene carbonate), poly (iminocarbonate), copoly(ether-esters), polyalkylene oxalates, polyphosphazenes, polyiminocarbonates, and aliphatic polycarbonates. Biomolecules such as heparin, fibrin, fibrinogen, cellulose, starch and collagen are typically also suitable. Examples of biostable polymers include Parylene®, Parylast®, polyurethane (for example, segmented polyurethanes such as Biospan®), polyethylene, polyethylene terephthalate, ethylene vinyl acetate, silicone and polyethylene oxide.

Therapeutic substances can include, but are not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon, genetically engineered epithelial cells, and dexamethasone. In other examples the therapeutic substance is a radioactive isotope for implantable device usage in radiotherapeutic procedures. Examples of radioactive isotopes include, but are not limited to, phosphoric acid ($H_3P^{32}O_4$), palladium ($Pd^{103}$), cesium ($Cs^{131}$), and iodine ($I^{125}$). While preventative and treatment properties of the foregoing therapeutic substances or agents are well-known to those of ordinary skill in the art, the substances or agents are provided by way of example and are not meant to be limiting. Other therapeutic substances are equally applicable for use with the disclosed methods and compositions.

While particular embodiments of the present invention have been shown and described, it will be clear to those of ordinary skill in the art that changes and modifications can be made without departing from this invention in its broader aspects and, therefore, the appended claims are to encompass within their scope all such changes and modifications as fall within scope of this invention.

What is claimed is:

1. A method of modifying a stent surface, comprising:
   applying a first charge to a stent; and
   applying a second charge to an electrode positioned in close proximity to the stent so that an electric discharge from the electrode produces a pit on a surface of the stent, the pit having an undercut.

2. The method of claim 1, wherein the stent and the electrode are submerged in a tank holding a dielectric fluid.

3. The method of claim 2, additionally comprising circulating the dielectric fluid in the tank.

4. The method of claim 2, additionally comprising circulating the fluid in a gap between the stent and the electrode to flush away substrate particles between the electrode and the stent.

5. The method of claim 1, additionally comprising rotating the stent about a longitudinal axis of the stent.

6. The method of claim 1, wherein the electrode is cylindrical in shape and the method additionally comprises rotating the electrode about a longitudinal axis of the electrode.

7. The method of claim 1, additionally comprising moving the electrode so that the electrode revolves around an axis of the stent.

8. The method of claim 1, additionally comprising positioning the electrode inside of the stent and rotating the electrode about a longitudinal axis of the stent.

9. The method of claim 1, wherein the length of the electrode is shorter than the length of the stent.

10. The method of claim 1, wherein the electrode is positioned on the inside of the stent so that the pit is produced on an inner surface of the stent.

11. The method of claim 1, wherein the electrode is positioned on the outside of the stent so that the pit is produced on an outer surface of the stent.

12. The method of claim 1, further comprising applying a coating to the surface of the stent.

13. The method of 12, wherein the coating includes a drug and/or a polymer.

14. The method of claim 1, further comprising positioning the stent on a mandrel, wherein the mandrel is in electrical communication with a power source.

* * * * *